United States Patent [19]

Gabel et al.

[11] Patent Number: 4,538,007

[45] Date of Patent: Aug. 27, 1985

[54] PROCESS FOR THE SIMULTANEOUS RECOVERY OF 4-HYDROXY-DIPHENYL AND 4,4'-DIHYDROXYDIPHENYL

[75] Inventors: Eike Gabel, Cologne; Heinz U. Blank; Horst Behre, both of Odenthal, all of Fed. Rep. of Germany

[73] Assignee: Bayer Aktiengesellschaft, Leverkusen, Fed. Rep. of Germany

[21] Appl. No.: 573,990

[22] Filed: Jan. 26, 1984

[30] Foreign Application Priority Data

Feb. 1, 1983 [DE] Fed. Rep. of Germany ....... 3303220

[51] Int. Cl.³ ...................... C07C 37/68; C07C 37/84
[52] U.S. Cl. .................................... 568/751; 568/753
[58] Field of Search ............... 568/751, 753, 748, 750, 568/749

[56] References Cited

U.S. PATENT DOCUMENTS

| 1,885,176 | 11/1932 | Britton et al. | 568/748 |
| 1,887,227 | 11/1932 | Britton et al. | 568/748 |
| 3,993,700 | 11/1976 | Smith et al. | 568/748 |
| 4,366,329 | 12/1982 | Raynolds | 568/753 |

FOREIGN PATENT DOCUMENTS 54-112844 9/1979 Japan ................... 568/738

OTHER PUBLICATIONS

Chemical Abstracts, Band 92, No. 5,4., Feb. 1980, Seite 747, No. 41563d, Columbus, Ohio, USA and JP-A-79 112 844, (Sanko Kagaku K.K.), 4/09/1979.

*Primary Examiner*—Werren B. Lone
*Attorney, Agent, or Firm*—Sprung, Horn, Kramer & Woods

[57] ABSTRACT

4-Hydroxydiphenyl (mono-OD) and 4,4'-dihydroxydiphenyl (DOD) are obtained simultaneously from a mixture which contains these two substances, if such a mixture is treated with an aqueous alkali, and the resulting solution and the solid phase formed are separated at a temperature from $-28°$ C. to $+40°$ C. and the solution and the solid phase are acidified separately in order to form the free mono-OD and DOD. Mono-OD and DOD can be present in the starting mixture in the free form or in the form of the alkali metal phenolates. After formation of the alkali metal phenolates, where this is required, the aqueous alkali still contains 1–15 mol of alkali metal hydroxide per mol of the diphenyl compounds. The concentration of alkali metal hydroxide should be 4–25% by weight, relative to the amount of water present. In this process, it is also possible to employ industrial mixtures of the alkali melts of the associated diphenyl-sulphonic acids.

17 Claims, No Drawings

PROCESS FOR THE SIMULTANEOUS RECOVERY OF 4-HYDROXY-DIPHENYL AND 4,4'-DIHYDROXYDIPHENYL

The present invention relates to a process for the simultaneous recovery of 4-hydroxydiphenyl (mono-OD) and 4,4'-dihydroxydiphenyl (DOD) from a mixture which contains the two substances, by treating such a mixture with an aqueous alkali.

Dihydroxy-diphenyls are used, for example, as a starting material for high-grade condensation polymers, such as polycarbonates, polyesters and powder formulations, the property of high-temperature stability being particularly noteworthy (German Offenlegungsschrift No. 3,031,094). Owing to the structural similarity, monohydroxydiphenyls can be employed as chain terminators for regulating the molecular weights. Dihydroxy-diphenyls are also used as intermediate products for pharmaceutical products, and as stabilisers and antioxidants for rubbers, oils and polymers. 4-Hydroxydiphenyls (p-phenyl-phenols) are used as intermediate products for the preparation of surface-coating resins, non-ionic emulsifiers and plant protection agents (Ullmanns Enzyklopädie der technischen Chemie (Ullmanns Encyclopaedia of industrial chemistry), 4th edition, volume 18, page 219).

An important route for the preparation of mono-OD and DOD starts from the diphenyl-4-sulphonic acid or the diphenyl-4,4'-disulphonic acid, which are converted to mono-OD and DOD, respectively, with the aid of an alkali melt, the sulpho group being exchanged for the hydroxyl group (German Offenlegungsschrift No. 3,031,094). The sodium salts of the stated sulphonic acids are frequently employed for this alkali melt, the salts being obtained afer sulphonation of diphenyl with excess sulphuric acid, dilution of the sulphonation mixture with water and partial neutralisation with sodium hydroxide solution or salting out with sodium chloride, followed by filtration and drying.

While DOD can be prepared by the stated route so that only small amounts, if any, of mono-OD have to be separated off, in the preparation of mono-OD the sulphonation of diphenyl can be carried out economically only in a manner such that a substantial amount of diphenyldisulphonic acid is formed in addition to the desired diphenyl-monosulphonic acid.

There has therefore been no lack of attempts to obtain the two stated substances in pure or at least concentrated form. Industrialy useful methods for the purification of substances or for the separation of mixtures of substances must be easy to carry out and at the same time give a highly selective separation. Such separation methods include, for example, distillation or rectification, sublimation, liquid/liquid extraction, crystallisation from solution or melt, and diffusion separation methods. However, the application of such separation methods to the separation and recovery of mono-OD and DOD is restricted by the similarity of these two compounds in their chemical and physical properties. Furthermore, unfavourable properties of the substances make certain separation methods unsuitable; thus, for example, separation by sublimation, distillation or crystallisation from the melt is difficult owing to the unfavourably high sublimation point and melting point. Because of these difficulties, the number of separation methods proposed in the literature is therefore small, in spite of the long-standing desire to purify the stated substances.

For example, Japanese Patent Application No. 56-92236 (1981) proposes separating mono-OD and DOD by a method in which an aqueous solution of these phenols in an alkali solution is extracted with a water-immiscible alcohol or ketone under elevated pressure, mono-OD passing into the organic phase, as free phenol. In this method, even small amounts of mono-OD require a substantial amount of organic solvent, so that this process is uneconomical and cannot be used for mixtures containing a large amount of mono-OD.

German Offenlegungsschrift No. 3,107,473 (equivalent to GB No. 2,071,090) proposes removing mono-OD from an alkaline solution of the stated phenolates in water by adsorption on active carbon. In this case, too, only small amounts of mono-OD can be removed; no information at all is given concerning a preparative recovery of this mono-OD which has been separated off.

Furthermore, Japanese Patent Application No. 54-112844 (1979) discloses that the alkali melt of diphenylsulphonic acid can be steered in the direction of the mono-OD so that the excess sodium hydroxide required for this purpose is brought into solution by the addition of as little water as possible, in order to separate it off from the mono-OD, and, if appropriate after concentration, to recycle it to the alkali melt. This process is used in the same manner when DOD is to be obtained from the diphenyl-4,4'-disulphonic acid, a very highly concentrated sodium hydroxide solution likewise being separated off from the remaining DOD and being recycled. In this procedure, however, mono-OD or DOD is always present individually, and no separation of the components takes place.

Since no satisfactory separation methods were found at the stage of the hydroxydiphenyls, separation at the stage of the diphenyl-sulphonic acids was also attempted. Such separations via the copper or sodium salts in combination with a separation of the free sulphonic acids (Gazz. Chim. Ital. 78, 435–440 (1948)) or via the ammonium salts (Czech Pat. No. 181,835) have been described, the salts of the diphenyl-monosulphonic acid being separated from the salts of the diphenyl-disulphonic acid. However, owing to the relatively good solubility of the salts of these sulphonic acids, such separation methods entail large losses and are therefore disadvantageous for industrial use.

The stated separation processes at the stage of the sulphonic acids require, between the sulphonation of diphenyl and the alkali melt of the sulphonic acids, an additional process step in which, furthermore, organic material in the form of diphenyl-sulphonic acid or diphenyl-disulphonic acid is lost with the waste water and at the same time pollutes this waste water. The precondition for the recovery of mono-OD and DOD, which does not have these disadvantages, is therefore a separation at the stage of the hydroxy-diphenyls.

Against the background of the prior knowledge, it was therefore surprising and not foreseeable that it would be possible to find process conditions which not only enable purification or concentration of mono-OD or DOD but permit the recovery of the two substances simultaneously in pure or concentrated form.

A process for the simultaneous recovery of 4-hydroxydiphenyl (mono-OD) and 4,4'-dihydroxydiphenyl (DOD) from a mixture containing the two substances in the free form or in the form of the alkali metal phenolates has been found, which is characterised in that such a mixture is treated with an amount of aqueous alkali such that after formation of the alkali metal phenolates, where this is required, 1–15 mol of alkali metal hydroxide per mol of the diphenyl compound are present and the concentration of alkali metal hydroxide is 4–25% by weight, relative to the amount of water present, the resulting solution, which essentially contains the DOD, is separated from the resulting solid phase, which essentially contains the mono-DOD, at a temperature from −28° C. to +40° C., and the solution and the solid phase are acidified separately in order to form the free mono-OD and the free DOD.

The aqueous solution of the hydroxide of an alkali metal, preferably of sodium or of potassium, may be mentioned as aqueous alkali. Of course, it is also possible to employ mixtures of alkali metal hydroxides. In accordance with the invention, mixtures of mono-OD and DOD are mixed with such an excess of alkali solution that 1–15 mol, preferably 3–10 mol, of the alkali metal hydroxide are present per mol of diphenyl compound employed, in the form of mono-OD or of DOD. In the case in which the mono-OD and the DOD are employed in the form of the free phenols, the alkali metal hydroxide required for the formation of the phenolates must be employed in addition. In accordance with the invention, the concentration of the alkali metal hydroxide after the formation of the alkali metal phenolates, where this is required, is 4–25, preferably 8–20, particularly preferably between 8 and 15, % by weight of alkali metal hydroxide, relative to the amount of water present in the reaction mixture.

The treatment, according to the invention, of the mixture containing mono-OD and DOD is carried out at room temperature to elevated temperature, for example at 15°–100° C. It is also possible to use temperatures outside this range.

The reaction mixture is then separated at a temperature from −28° C. to +40° C., preferably −15° C. to +35° C., particularly preferably −10° C. to +30° C. This procedure gives a solid phase, which essentially contains the mono-OD, and a solution, which essentially contains the DOD. The separation is effected in a known manner, for example by filtration or by centrifuging.

The filtration residue contains up to 99% of the mono-OD employed, which, relative to 100 parts by weight, contains, for example, 5, in many cases less than 1, parts by weight of DOD. If the starting mixture used only contained 1 part by weight of DOD before being used in the process according to the invention, the content of DOD in the filtration residue obtained according to the invention can be less than 0.5 part by weight per 100 parts by weight of mono-OD. The purity of the filtration residue can be increased further, for example, by washing with an alkali solution, the concentration of which is preferably the same as the concentration of the alkali solution employed in accordance with the invention for the treatment. If it is desired that the DOD present in the filtrate has a particularly high purity, this can be achieved by keeping the solubility of the mono-OD alkali metal salt low, for example by increasing the concentration of the alkali solution or by decreasing the filtration temperature. It will then be possible for the mono-OD thus obtained to be contaminated with DOD to a greater extent.

The filtrate contains 70 to 95% by weight of the free alkali solution employed. It also contains the remainder of the DOD employed and small amounts of mono-OD, which do not exceed, for example, 25% of the sum of DOD and mono-OD in the solution. If it is desired to separate off a mono-OD which is virtually DOD-free, and for this purpose, for example, the mixture is diluted to a greater extent or the residue is washed with alkali solution, the mono-OD fraction can also exceed 25% of the sum of mono-OD and DOD in the solution. Using the product obtained from the filtrate, it is possible to carry out a further separation directly. In many cases, however, the amount of mono-OD is less than 10%, relative to the total amount of DOD and mono-OD in the solution. Even in extreme cases in which, in addition to a predominant proportion of mono-OD, only a very small amount of DOD is present in the starting material, a substantial concentration of DOD, to several times its percentage in the starting material, is achieved in the filtrate; for example, a starting mixture containing 11% of DOD, relative to the sum of mono-OD and DOD, can be separated so that the filtrate obtained contains 94% of DOD, relative to the sum of mono-OD and DOD.

In the process according to the invention, mixtures of mono-OD and DOD in the free form or in the form of their alkali metal salts in a ratio from 1:100 to 100:1, preferably 5:100 to 100:5, particularly preferably 10:100 to 100:10, can be employed.

The mixtures which can be employed according to the invention and are to be separated in order to recover mono-OD and DOD simultaneously can furthermore contain alkali metal sulphate, for example 0 to 5 mol of alkali metal sulphate per mol of diphenyl compounds present, and, if appropriate, also alkali metal sulphite, for example 0 to 1 mol of alkali metal sulphite per mol of phenolate group present. In principle, a content of more than 1 mol of alkali metal sulphite per mol of phenolate group also permits the process according to the invention to be carried out successfully. In general, however, the amount of any alkali metal sulphite present is about 1 mol per mol of phenolate group, since this is the amount obtained when sulphonates are subjected to an alkali melt to give the corresponding phenolates.

This also gives rise to the possibility of employing, in the process according to the invention, mixtures which are obtained from the alkali melt of the corresponding diphenyl-sulphonic acids. In such industrial mixtures, an adequate amount of alkali metal hydroxide is generally present, so that it is sufficient merely to add water to such mixtures from the alkali melt in order to establish the concentrations and proportions according to the invention. This use of industrial mixtures from the alkali melt of diphenyl-sulphonic acid salts therefore represents a preferred variant of the process according to the invention.

To obtain free mono-OD and free DOD, the filtration residue dissolved in water, and the filtrate, respectively, are acidified. For this purpose, the pH value is adjusted to a maximum of 8, for example 7 to 1. The acidification can, in principle, be carried out with any desired acid which has a greater acid strength than that of the phenolic groups of the mono-OD or of the DOD. From economic considerations, however, simple and cheap mineral acids, such as hydrochloric acid, sulphuric acid, nitric acid or phosphoric acid, preferably hydrochloric acid or sulphuric acid, will generally be chosen.

Where higher requirements in respect of the purity of the mono-OD or DOD make further purification steps necessary, these may follow the process according to the invention or be incorporated into the same. For example, the following may be mentioned in this context: subsequent crystallisation from organic solvents, repeated dissolution and reprecipitation of the phenolates with mineral acids, clarification of the phenolate solutions with active carbon (this last-mentioned possible method of purification, for example, also within the process according to the invention, before precipitation with an acid) and, in the case of very high purity requirements, also fine distillation in a high vacuum or sublimation, if appropriate, under reduced pressure.

The process according to the invention has the following advantages:

1. The separation and simultaneous recovery of mono-OD and DOD can be used for a wide range of mixtures of mono-OD and DOD.

the invention, in order simultaneously to recover mono-OD and DOD.

EXAMPLE 1

A mixture of 85.1 g of 4-hydroxydiphenyl and 93.1 g of 4,4'-dihydroxydiphenyl was dissolved in 1633 g of 13.5% strength by weight sodium hydroxide solution by heating. After the solution had been cooled to 20° C., a crystalline precipitate was formed, and this was filtered off under suction.

Subsequent analysis by means of high-pressure liquid chromatography indicated that the residue contained 76.8 g of 4-hydroxydiphenyl and 3.3 g of 4,4'-dihydroxydiphenyl, and the filtrate contained 88.3 g of 4,4'-dihydroxydiphenyl and 3.4 g of 4-hydroxydiphenyl.

EXAMPLES 2-4

The experiment from Example 1 was repeated, the changes and results being shown in Table 1.

TABLE 1

| | Starting mixture | | Alkali solution | | In the residue | | In the filtrate | |
|---|---|---|---|---|---|---|---|---|
| Example | 4-Hydroxy-diphenyl (g) | 4,4'-Di—hydroxy-diphenyl (g) | Amount (g) | Concentration (% by weight) | 4-Hydroxy-diphenyl (g) | 4,4'-Di—hydroxy-diphenyl (g) | 4-Hydroxy-diphenyl (g) | 4,4'-Di—hydroxy-diphenyl (g) |
| 2 | 119.2 | 55.9 | 2029 (NaOH) | 12.4 | 116.0 | 1.8 | 3.2 | 54.1 |
| 3 | 153.2 | 18.6 | 2024 (NaOH) | 12.1 | 149.7 | 0.5 | 3.5 | 18.1 |
| 4 | 153.2 | 18.6 | 1442 (KOH) | 23.7 | 149.4 | 1.7 | 3.8 | 16.9 |

2. The separation takes place with high selectivity in spite of the great similarity of the two compounds. As stated above, it is possible, by choosing the conditions within the scope of the process according to the invention, to influence the selectivity so that either the one or the other of the two compounds can be obtained in particularly high purity.

3. In the simultaneous recovery of mono-OD and DOD according to the invention, substance losses are substantially avoided.

4. The process according to the invention is carried out in an aqueous medium and does not require complicated apparatus; hence, it is simple and economical to carry out industrially.

5. The process according to the invention can be freely incorporated into the customary industrial process for the preparation of hydroxy-diphenyls, characterised by sulphonation of diphenyl, conversion of the sulphonic acids to the alkali metal salts, and a final alkali melt.

In particular, the last-mentioned advantage enables hydroxy-diphenyl compounds to be prepared by novel routes. By means of variations, which are familiar to one skilled in the art, in the reaction conditions during the sulphonation of diphenyl with sulphuric acid (by suitable choice of the reaction temperature, of the molar ratio of $H_2SO_4$ to diphenyl, of the sulphuric acid concentration and/or the reaction time), any desired mixtures of diphenyl-sulphonic acid and diphenyl-disulphonic acid can be prepared, substantially complete conversion of diphenyl being achieved. Such mixtures of diphenyl-sulphonic acid can be converted directly to the corresponding mixtures of the alkali metal salts of the hydroxy-diphenyl compounds by means of an alkali melt, and can be separated in the manner according to

EXAMPLE 5

A mixture comprising 234.0 g of diphenyl-4-sulphonic acid Na salt, 30.8 g of diphenyl-4,4'-disulphonic acid $Na_2$ salt, 101.4 g of $Na_2SO_4$ and 3.8 g of $H_2O$, which initially contained 1 mol of diphenyl, as well as 280 g of 100% strength NaOH and 168 g of $H_2O$, were heated to 320° C. for 15 hours in a nickel autoclave, under an autogenous pressure of 37 bars. The mixture was diluted with 1546 g of $H_2O$ and filtered at 20° C.

The residue moist with sodium hydroxide solution was dissolved in 3000 ml of $H_2O$, and the solution was neutralised with HCl until the pH value was 7. After the solution had been cooled to room temperature, the solid phase was filtered off under suction and washed salt-free with water. The filtrate was also neutralised analogously. The products which had been filtered off under suction were dried at 70° C. in a vacuum drying oven.

The following products were obtained:

153.2 g of product I from the filter residue, containing:

99.6% by weight of 4-hydroxydiphenyl[1] = 89.7% of theory, relative to diphenyl, 0.1% by weight of 4,4'-dihydroxydiphenyl[2] = 0.1% of theory, relative to diphenyl, and 0.3% by weight of diphenyl-4-sulphonic acid = 0.2% of theory, relative to diphenyl and 14.7 g of product II from the filtrate, containing:

8.6% by weight of mono-OD = 0.75% of theory, relative to diphenyl, and 91.4% by weight of DOD = 7.2% of theory, relative to diphenyl.

[1] abbreviated to mono-OD below;
[2] abbreviated to DOD below;

EXAMPLES 6–7

The experiment from Example 5 was repeated, except that the mixture was diluted with a total of 3475 ml or with 1095 mol of $H_2O$ respectively.

TABLE 2

| Ex- | ml of $H_2O$ | Composition, % by weight | | | |
|---|---|---|---|---|---|
| | | Product I | | Product II | |
| ample | for working up | Mono-OD | DOD | Mono-OD | DOD |
| 6 | 3475 | 99.9 | 0.1 | 52.0 | 48.0 |
| 7 | 1095 | 94.7 | 5.2 | 0.9 | 99.1 |

EXAMPLE 8

The experiment from Example 5 was repeated, the following mixture being employed in the alkali melt: 210 g of diphenyl-4-sulphonic acid Na salt, 72 g of diphenyl-4,4'-sulphonic acid $Na_2$ salt, 111 g of $Na_2SO_4$, 265 g of NaOH and 176 g of $H_2O$.

After the reaction, 1300 ml of water were added and the separation was carried out. The products obtained after working up are described in Table 3.

EXAMPLE 9

The experiment from Example 5 was repeated, the following mixture being employed in the alkali melt: 64 g of diphenyl-4-sulphonic acid Na salt, 268 g of diphenyl-4,4'-disulphonic acid $Na_2$ salt, 320 g of $Na_2SO_4$, 437 g of NaOH and 293 g of $H_2O$.

After the reaction, 2350 ml of water were added and the separation was carried out. The products obtained after working up are described in Table 3.

TABLE 3

| | Composition (% by weight) | | | |
|---|---|---|---|---|
| | Product I | | Product II | |
| Example | Mono-OD | DOD | Mono-OD | DOD |
| 8 | 99.5 | 0.5 | 5.2 | 94.8 |
| 9 | 93.5 | 6.5 | 3.3 | 96.7 |

What is claimed is:

1. A process for simultaneously separating 4-hydroxydiphenyl and 4,4'-dihydroxydiphenyl from a mixture containing an alkali metal salt thereof which comprises adjusting the water and alkali metal content of said mixtures such that it contains a stoichiometric excess of 1–15 mols of alkali metal hydroxide per mol of the combined amount of 4-hydroxydiphenyl or 4,4'-dihydroxydiphenyl or the corresponding phenolate thereof and the alkali metal hydroxide is present in an amount of 4–25% by weight based upon the weight of the water, whereby to form a solid phase which contains a predominant amount of said 4-hydroxydiphenyl or the corresponding phenolate and a solution phase which contains a predominant amount of said 4,4'-dihydroxydiphenyl or the corresponding phenolate, separating said solution phase and said solid phase at −28° C. to +40° C. and acidifying at least one of said phases.

2. A process according to claim 1, wherein said 4-hydroxydiphenyl and said 4,4'-dihydroxydiphenyl are present in a mixture in the form of free phenols and are converted to the corresponding phenolates by contact with an alkali metal hydroxide aqueous solution.

3. A process according to claim 1, both said solid phase and said solution phase are acidified.

4. A process according to claim 1, wherein said solution phase is acidified.

5. A process according to claim 1, wherein said solid phase is acidified.

6. A process according to claim 1, wherein an excess of 3–10 mols of alkali metal hydroxide are employed per mol combined amounts of 4-hydroxydiphenyl and 4,4'-dihydroxydiphenyl or corresponding phenolates.

7. A process according to claim 1, wherein the alkali metal hydroxide of said solution is present in an amount of 8–20% by weight based upon the weight of the water.

8. A process according to claim 1, wherein the alkali metal hydroxide is sodium hydroxide or potassium hydroxide.

9. A process according to claim 1, wherein the separation of the solid phase and solution phase is performed at a temperature of −15° to +35° C.

10. A process according to claim 1, wherein the separation of the solid phase and the solution phase is effected at a temperature of −10° to +30° C.

11. A process according to claim 1, wherein the mixture which is treated contains 4-hydroxydiphenyl and 4,4'-dihydroxydiphenyl in a weight ratio of 1:100 to 100:1.

12. A process according to claim 1, wherein the mixture which is treated contains 4-hydroxydiphenyl and 4,4'-dihydroxydiphenyl in a weight ratio of 5:100 to 100:5.

13. A process according to claim 1, wherein the mixture which is treated with alkali metal hydroxide is one to which an alkali metal sulphate or alkali metal sulphite is added.

14. A process according to claim 1, wherein an aqueous alkali metal hydroxide solution is added to said mixture containing 4-hydroxydiphenyl and 4,4'-dihydroxydiphenyl or corresponding phenolates at a temperature of 15° to 100° C.

15. A process according to claim 1, wherein said 4-hydroxydiphenyl and 4,4'-dihydroxydiphenyl are present in the form of a corresponding alkali metal phenolate in an alkali melt of the corresponding diphenyl-sulphonic acids.

16. A process according to claim 1, wherein the alkali metal hydroxide of said solution is present in an amount of 8–15% by weight based upon the weight of the water.

17. A process according to claim 1, wherein the mixture which is treated contains 4-hydroxydiphenyl and 4,4'-dihydroxydiphenyl in a weight ratio of 10:100 to 100:10.

* * * * *